United States Patent [19]

Rinne et al.

[11] 4,351,327
[45] Sep. 28, 1982

[54] DEVICE FOR CONNECTION TO A RESPIRATORY GAS LINE

[75] Inventors: Gerhart Rinne, Stockelsdorf; Ulrich Heim, Reinfeld, both of Fed. Rep. of Germany

[73] Assignee: Drägerwerk Aktiengesellschaft, Fed. Rep. of Germany

[21] Appl. No.: 225,538

[22] Filed: Jan. 16, 1981

[30] Foreign Application Priority Data

Feb. 2, 1980 [DE] Fed. Rep. of Germany ....... 3007755

[51] Int. Cl.$^3$ ............................................ A61M 16/00
[52] U.S. Cl. ........................... 128/200.14; 128/205.24; 128/200.19; 251/149.9; 251/89.5; 137/637.1; 137/614.06; 137/884; 74/483 K
[58] Field of Search ....................... 128/200.13, 200.14, 128/200.19, 200.21, 203.12, 205.24; 251/149.6, 149.9, 89.5; 137/614.06, 599.1, 637.1, 884; 74/483 K

[56] References Cited

U.S. PATENT DOCUMENTS

| | | | |
|---|---|---|---|
| 3,077,191 | 2/1963 | Stanton | 128/200.13 |
| 3,693,655 | 9/1972 | Frisk | 251/149.9 |
| 3,703,172 | 11/1972 | Hay | 128/200.13 |
| 3,792,612 | 2/1974 | Lammel et al. | 137/637.1 |
| 3,831,599 | 8/1974 | Needham | 128/203.12 |
| 4,058,120 | 11/1977 | Caparrelli et al. | 128/203.12 |

FOREIGN PATENT DOCUMENTS 2060403 5/1981 United Kingdom ........... 128/200.14

OTHER PUBLICATIONS

Airco, Ohio Medical Products-Unitrol Anesthesia Machine, Form No. 9906, 1978 Catalog.

*Primary Examiner*—Henry J. Recla
*Attorney, Agent, or Firm*—McGlew and Tuttle

[57] ABSTRACT

A device for connection to a respiratory gas line, particularly a narcosis apparatus, comprising, a terminal board having a first engagement surface thereon and a respiratory gas line defined therein with a first pair of connecting lines extending from the respiratory gas line to the engagement surface. An equipment unit for example, an evaporator or flowmeter is provided for connection to the respiratory gas line and has an adapter with a second engagement surface and a second pair of connecting lines extending to the second engagement surface. Structure is provided to align the first and second pairs of connecting lines to each other when the first and second engagement surfaces are engaged with each other to establish communication between the respiratory gas line and the second pair of connecting lines. A valve is also provided either in the first pair of connecting lines or in the second pair of connecting lines. The valve in the first pair of connecting lines takes the form of a bypass line bypassing the first pair of connecting lines.

14 Claims, 7 Drawing Figures

DEVICE FOR CONNECTION TO A RESPIRATORY GAS LINE

FIELD AND BACKGROUND OF THE INVENTION

The present invention relates in general to add-on equipment for respiratory devices and in particular to a new and useful narcosis apparatus with equipment units such as evaporators, flowmeters and the like which can selectively be connected to a terminal board and have connecting lines for gaseous or vaporous media and which can be coupled to corresponding, flush alignable connecting lines in the terminal board.

Narcosis apparatus of known design, such as shown in DE-AS 22 43 733, for example, comprise a frame for the detachable attachment of narcosis units which can be plugged into appropriate attachment fields of connections under a building block principle. The connection between the connecting lines in the narcosis units and the connecting lines in the frame is established via fitting plug connection elements which, at the same time, effect a support of the units. When removing a narcosis unit, it is possible to establish, through appropriate valves in the outlet and inlet plug connection elements, a bypass connection between the inlet and the outlet, within the connecting lines of the frame when the plugs of a unit are not plugged in. These valves establish a bypass canal.

A mixing unit with selector valve is also known and designed as a built-in unit. By means of this unit the respectively desired narcosis unit can be connected to the respiratory air line while the other narcosis units are shut off.

This known design makes it possible to equip a frame of the built-in unit selectively with equipment units. The connection via plug connection elements, which also absorb support forces, proves difficult to use, particularly when several well spaced plug connections are involved. The sumultaneous establishment of the plug connections requires sensitive and precise handling if canting and possibly damage to the plug connections is to be avoided. This contradicts the requirement for simplest handling, also under conditions of stress. The selection of the various narcosis units by a selector switch also means additional equipmental expense and added susceptibility to trouble.

SUMMARY OF THE INVENTION

It is an object of the present invention to design a narcosis apparatus of the type described above, so that the attachment of the equipment units is possible simply and automatically, precluding incorrect connections. Moreover, the equipment units should communicate with each other and/or a terminal board, via a multiplicity of connecting lines while securely sealing the disconnect points without requiring sensitive handling when attaching these equipment units. A characteristic feature of the invention is that the equipment unit is attachable to the terminal board by means of a fitting adapter via plane, multiple flange surfaces in which the connecting lines of the equipment units and the connecting lines of the terminal board, end. A control device, which is operable by the plugged-in equipment unit, is also provided which controls control elements inside the equipment unit and/or inside the connecting lines of the terminal board. Such a design makes a simple attachment of the equipment units to the terminal board possible. Undesired switching operations can be automatically precluded by the control device operable of the invention, by the interaction of an equipment unit and a terminal board, so that operating safety, particularly, under conditions of stress such as during a medical emergency, is materially improved.

It is advantageous for the control device on the equipment unit of the invention, to have a control lever which can assume an "on" position and a release position for the desirable automatic control thereof. An extension of the control lever engages a control element through a fitting recess in the terminal board. In its release position, connecting lines of the terminal board are blocked or bypassed, and, after the equipment unit is plugged in, the control lever can be brought into its "on" position in which the respective equipment unit is inserted into the flow path in the intended manner.

Where units having their own adjustment element are involved, such as in an evaporator, it may be expedient, furthermore, for the control lever to have a blocking element which, in the release position of the control lever, locks the adjustment element of the equipment unit in its "zero" position, or "full off" position, shutting off the flow through the equipment unit via valves. It is thus assured, in this manner, that the adjustment element is in its "zero" position when the equipment unit is being plugged in or unplugged.

Another improvement can be made, if applicable, in that the engaging end of the control lever and the seating recess in the terminal board for the lever are of such shape that engagement is possible in the release position of the control lever only. In conjunction with the above described element, an additional safety is thereby achieved.

According to another feature of the invention, attachment points for the equipment units on the terminal board are expediently aligned with appropriate bypass connections in the connecting lines and operable by the control lever so that, in its release position, the connecting lines of the terminal board leading to the equipment unit are bridged by being bypassed and, in its "on" position, are connected to the respective connecting lines of the equipment unit. Such a structure makes possible either the plugging in or the unplugging of equipment units when the overall apparatus is in operation or when it is in a preparatory condition.

In this connection it may be expedient to provide a safety inside the terminal board, controllable by the control lever of the equipment unit so that "on" position of the control lever of one equipment unit blocks an actuation of the control lever of another equipment unit in the same direction. This means that when several identical equipment units, such as evaporators, are involved, only one equipment unit at a time can be brought into the "on" position and inserted into the flow path. This is another safety feature to prevent handling errors.

In one advantageous embodiment the equipment unit may have an adapter fitting the terminal board section, which may also form, with this adapter, a suspension fastening to the terminal board in an advantageous manner. Such a fastening assures simple handling when plugging in and unplugging without canting the multiple flange surfaces which, in in addition, can be kept under an appropriate preload, favoring a sealing action, due to the natural weight of the suspended equipment units.

Another advantage can be gained by locating the multiple flange surfaces in different planes of the terminal board, such as at right angles to each other or by positioning them obliquely. This simplifies the plumbing in the invention.

In another embodiment of the narcosis apparatus a slide element is used instead of a control lever, which projects out of the terminal board, and which is movable within the terminal board and has two manually separated recesses for the establishment of flow-through connections which communicate with the connecting lines in accordance with the lengthwise orientation of the slide element so that, when plugging in or unplugging an equipment unit, the connecting lines are either connected to the equipment unit or a bypass is established.

Such a design is expedient particularly for equipment units having no adjustment element of their own. It results in a simple and uncluttered overall construction.

In another embodiment of the invention, the control lever may be designed as a chucking element of multiple flange surfaces. This means that a clamping force is exerted on the multiple flange surfaces at the same time the control lever is transferred from the release position into the "on" position.

By applying the features of the invention, a narcosis apparatus with modularly connectable equipment units is created which achieves a reliable connection between terminal board and equipment unit in multiple flange surfaces and which, in addition, offers great safety both against operating errors when plugging in several identical equipment units under operating conditions and when plugging in equipment units with adjustment elements. The arrangement further makes possible optimum and uncluttered wiring and/or plumbing inside the equipment units and in the terminal board. The control device, operable by the plugged in equipment unit, obviates a selector switch inside the terminal board and the additional wiring/plumbing associated therewith.

Accordingly, another object of the present invention is to provide a device for connection to a respiratory gas line comprising, a terminal board having a first engagement surface thereon and a respiratory gas line defined therein with a first pair of connecting lines extending from the respiratory gas line to the first engagement surface, an equipment unit for connection to the repiratory gas line having an adapter with a second engagement surface and a second pair of connecting lines extending to the second engagement surface, alignment means on the adapter and terminal board for aligning the first and second pairs of connecting lines with each other when the first engagement surface is engaged with the second engagement surface, and control valve means in at least one of the equipment unit and terminal board for blocking flow in at least one of the first and second pairs of connecting lines.

A further object of the invention is to form the control valve means of a control element movable in the terminal board from a connection position for connecting a flow between the respiratory gas line and the first pair of connecting lines and a bypass position for bypassing the first pair of connecting lines.

A still further object of the present invention is to provide a device for connection to a respiratory gas line wherein the control element is rotatably mounted in the terminal board and a locking lever rotatable in the adapter and engageable with the control element to rotate the control element.

Another object of the invention is to provide a device for connection to a respiratory gas line wherein the control valve comprises a slide element mounted for movement in the terminal board for establishing communication between the first and second papers of connecting lines when the second engagement surface is engaged on the first engagement surface and for bypassing the first pair of connecting lines when the first and second engagement surfaces are not engaged with each other.

A further object of the invention is to provide a device for connection to a respiratory gas line which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
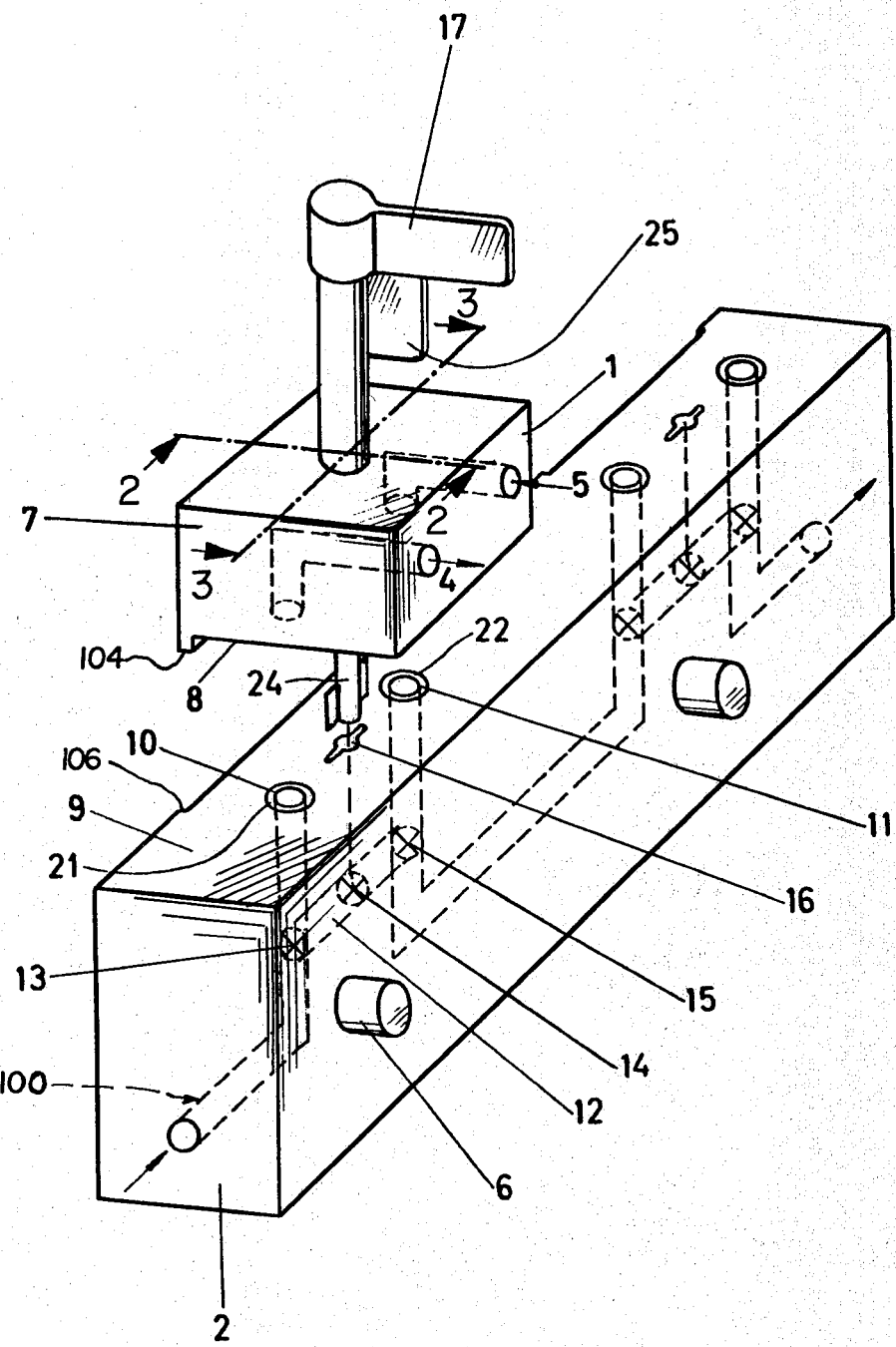
FIG. 1 is an isometric view of a terminal board with suspendable equipment unit; according to the invention.

Turning to the drawings in particular, the invention embodied therein comprises, a device for connection to a respiratory gas line shown generally at 100 in FIG. 1 which includes an equipment unit 1 which is connectable to a terminal board 2 containing the respiratory gas line 100.

Figure 2:
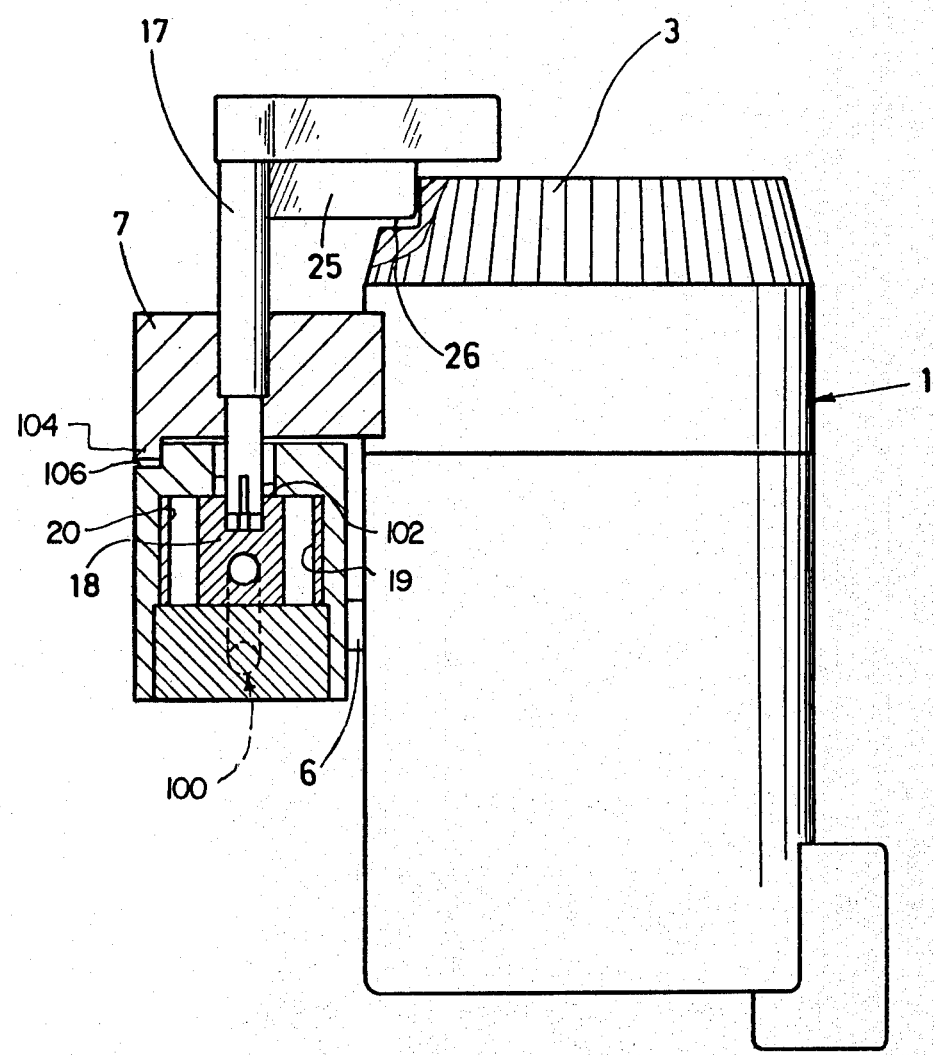
FIG. 2 is a view taken along line 2—2 of FIG. 1.

In FIGS. 1 and 2 the equipment unit 1 is shown, in the form of an evaporator. For clarity, only an adapter 7 of the equipment unit 1 is shown in FIG. 1. The evaporator body includes a turnable adjusting element, designed as capped wheel 3 which is visible in FIG. 2. Equipment 1 may also be a flowmeter or other device for connection to a respiratory gas line.

Inside the adapter 7 of the equipment unit 1 are connecting lines 4,5 ending in a plane, multiple flange surface 8. Opposite this multiple flange surface 8, on the terminal board 2, is another multiple flange surface 9 with connecting lines 10, 11 terminating in it. Elastic stops 6 on the terminal board 2 serve to support the plugged-in equipment units 1.

Figure 3:
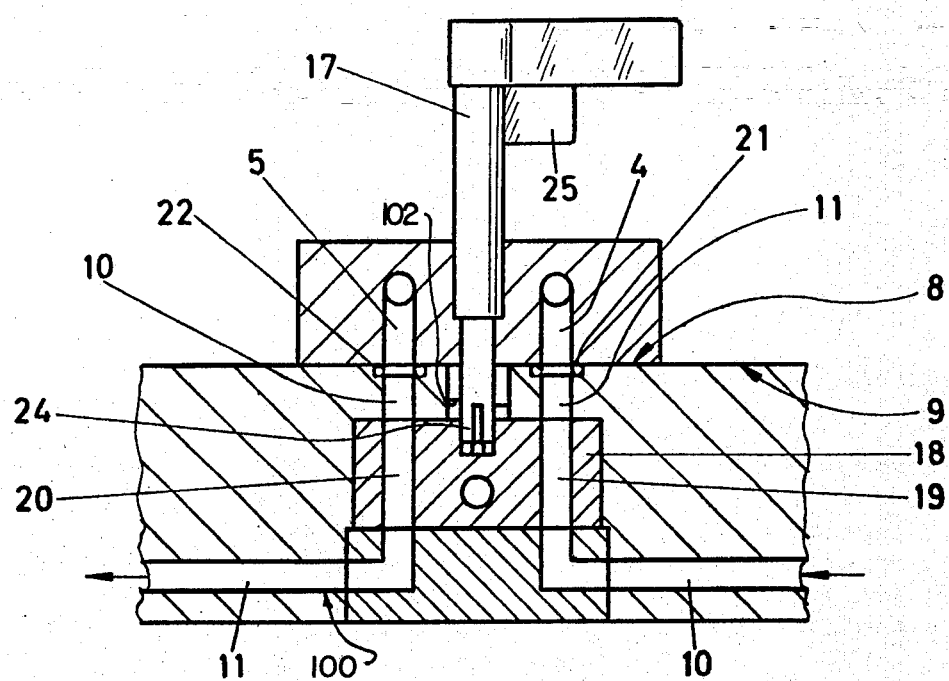
FIG. 3 is a view taken along line 3—3 of FIG. 1 showing the "on" position of the control lever.

Provided between the connecting lines 10, 11 in the terminal board 2 near the attachment point of the equipment unit 1, is a bypass line 12 which is controllable selectively via appropriate valve elements 13,14,15, the design of which will be explained below in greater detail. The valve elements serve to connect the evaporator or equipment unit 1, or bypass the equipment unit, by the positioning of a locking lever 17 engaging a recess 16 in the terminal board 2. The side view of FIG. 2 explains the design of the locking lever 17 which, penetrating the recess 16, engages a turnable control element or valve member 18 which has flow-through recesses 19, 20 which, in the "on" position shown in FIG. 3, are aligned with sections of the connecting lines 10,11 thus establishing a connection to the connecting lines 4,5 via the multiple flange surfaces 8, 9. Elastic O-ring seals 21 and 22 are disposed in the area of the mouth of the connecting lines 10,11 for improved sealing action to lines 4,5.

Figure 4:
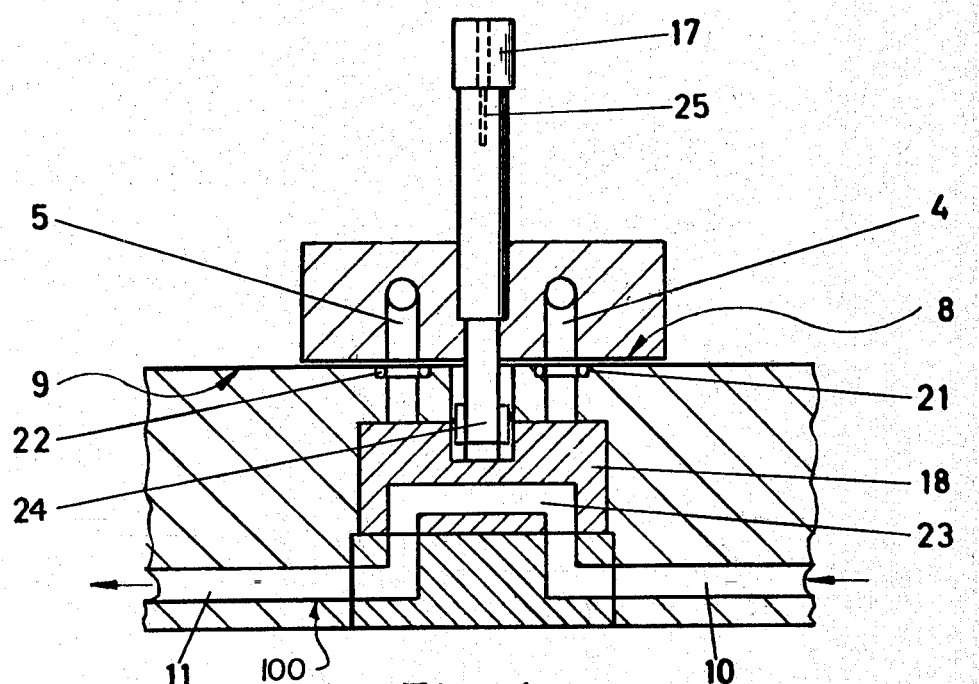
FIG. 4 is a view similar to FIG. 3 showing the release position of the control lever.

In FIG. 4 the release position of the locking lever 17 is shown, in which the control element 18 establishes the bypass connection between the connecting lines 10, 11 of the terminal board via a bypass canal 23 (schematically shown as line 12 in FIG. 1), in which the evaporator of the equipment unit 1, hooked up in a preparatory position, is not inserted in the respiratory gas line 100. The engaging end 24 of the control lever 17 is made to fit the contour of the recess 16 like a key in a key hole (see FIG. 1).

A protrusion 25 of lever 17 engaging, in the release position of the control lever 17 shown in FIG. 2, a corresponding open-rim recess 26 of the capped wheel 3, is located as a locking element, on the control lever 17. The effect of this locking element is that the control lever 17 can be brought into its release position, in which it can be inserted into the terminal board 2 through the recess 16 and in which the equipment unit 1 in its preparatory position can be hooked up, only if the adjusting element 3 is in its "zero" position to block flow in lines 4,5. When wheel 3 is turned, then lever 17 can be turned to connect lines 10, 11.

The recess 16 in terminal board 2 has a lower ledge 102. The wing portions are outwardly extending portions of engaging end 24 must move downwardly below this ledge 102 for the lever 17 to be rotatable to rotate the valve member 18. The protrusion 25 therefore must be aligned with the recess 26 in wheel 3 to permit sufficient downward movement of the locking lever 17 to move the end 24 past the ledge 102.

An alignment means is also provided either by the extension of the lever 17 into the recess 16 alone or additionally by use of an extension 104 on one end of the adapter 7 which fits into a recess 106 in the terminal board.

Figure 5:
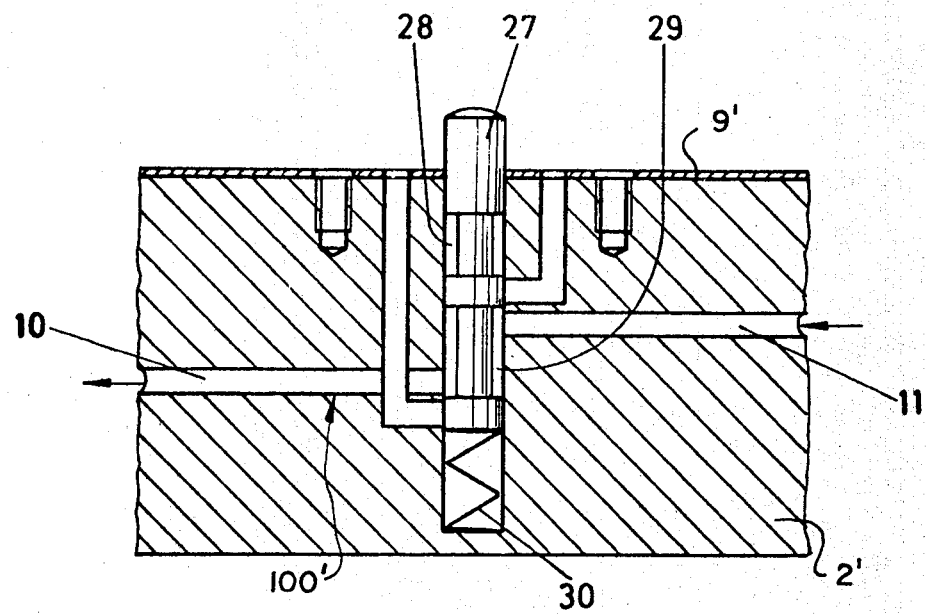
FIG. 5 is a sectional view similar to FIG. 3 of an alternate embodiment of the invention.
Figure 6:
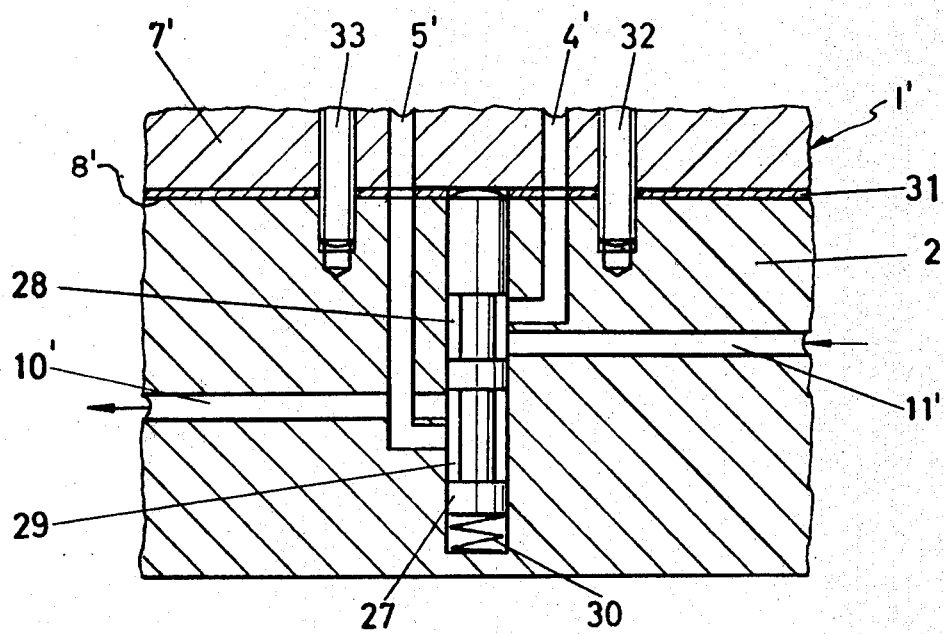
FIG. 6 is a sectional view similar to FIG. 5, showing an "on" position of the device.

In FIGS. 5 and 6 similar elements are designated with similar numbers having a prime. FIGS. 5 and 6 show an alternative embodiment without a control lever, but with a slide element 27 which is movable lengthwise in the terminal board 2' and which has at its periphery two mutually separated annular chambers which communicate with sections of the connecting line 10', 11' in the terminal board 2'. The slide element is biased by a helical compression spring 30 which causes the end portion of the slide element 27 to project out of the terminal board 2. In this position of the slide element 27 as shown in FIG. 5, the connecting lines 10', 11' are switched to bypass. A shift of the slide element 27 due to the plugging-in of the equipment unit 1' into the position shown in FIG. 6 brings about a flow-through connection of the connecting lines 10', 11' of gas line 100'.

To improve the sealing action, an elastic coating 31 is provided on the surface of the multiple flange surface 9' in this embodiment. The multiple flange surfaces 8', 9' are here pressed against each other by two tightening screws 32,33.

Figure 7:
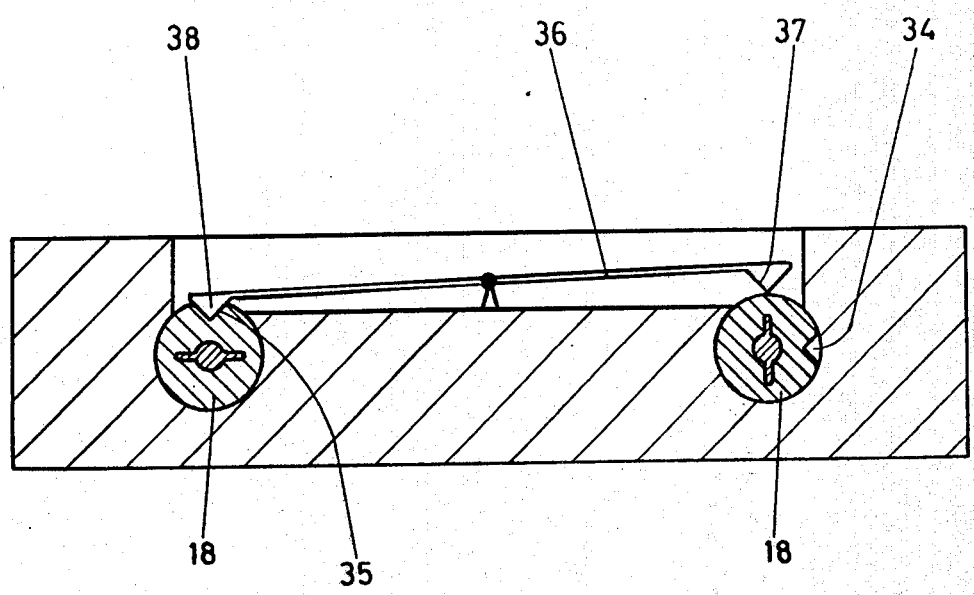
FIG. 7 is a transverse sectional view of a terminal board in the invention with mutual interlocking of the attachment points.

FIG. 7 shows an interlock system for identical equipment units in juxtaposed attachment points. Both control of valve elements 18 are provided with V-shaped recesses 34, 35. Supported against their periphery is a spring-loaded rocker 36 which has engagement wedges 37, 38. The right control element 18 has been brought into the "on" position due to the engagement of the control lever 17 of an equipment unit 1. This caused the engagement wedge 37 of the rocker 36 to be raised, and the engagement wedge 38 now to engage the V-shaped recess 35 so that an actuation of the left control element 18 in the same direction is prevented.

When hooking up an equipment unit 1 to this attachment point, therefore, only one preparatory position can be reached. Only after the equipment unit 1 on the right attachment point is completely shut off is it possible to actuate the control lever 17 on the equipment unit 1 in preparatory position into the "on" position.

While specific embodiments of the invention have been shown and described in detail to illustrate the application of the principles of the invention, it will be understood that the invention may be embodied otherwise without departing from such principles.

What is claimed is:

1. A device for connection to a respiratory gas line comprising:

a terminal board having a first engagement surface thereon and a respiratory gas line defined therein with a first pair of connecting lines extending from the respiratory gas line to the first engagement surface and a recess opening;

an equipment unit connectable to the respiratory gas line for receiving gas therefrom, treating the gas received and returning treated gas to the respiratory gas line, said unit having an adapter with a second engagement surface and a second pair of connecting lines extending to the second engagement surface for receiving and returning gas to and from said unit;

alignment means on said adapter and terminal board for aligning said first pair of connecting lines with said second pair of connecting lines when said first engagement surface is engaged with said second engagement surface;

a valve element movable in said terminal board from an "on" position for establishing flow in said first pair of connecting lines between said respirator gas line and said first engagement surface, and to an "off" position for establishing communication between said first pair of connecting lines and blocking communication of said first pair of connecting lines to said first engagement surface; and a control lever movably mounted in said adapter extendible through said recess opening into engagement with said valve element when said first and second engagement surfaces are engaged with each other to move said valve element.

2. A device according to claim 1, wherein said terminal board recess opening extends from said first engagement surface to said valve element for receiving said control lever.

3. A device according to claim 2, wherein said alignment means comprises said engagement end of said control lever extending into said recess opening in said terminal board.

4. A device according to claim 1, including an adjustment element movably mounted on said equipment unit movable from a first position blocking flow in said second pair of connecting lines to a second position, a blocking element connected to said control lever and engageable with said adjustment element to retain said adjustment element in its first position when said control lever is positioned to hold said valve element in its "off" position.

5. A device according to claim 1, wherein said control lever includes an engagement end, said recess in said terminal board being shaped to permit entry of said engagement end therethrough and into engagement with said valve element only when said valve element is in its "off" position.

6. A device according to claim 5, wherein said engagement end includes wing extensions, said recess in said terminal board being shaped to receive said engagement end and having a ledge below which said winged extensions must extend before said control lever can be moved to move said valve element.

7. A device according to claim 1, wherein said valve element is rotatably mounted in said terminal board and includes a bypass line defined therein for connecting said first pair of connecting lines to each other with said valve element in its "off" position and a pair of flow through lines connecting said respiratory gas line to said first pair of connecting lines at said first engagement surface with said valve element in its "on" position.

8. A device according to claim 1, wherein said terminal board includes a plurality of said first pair of connecting lines each for alignment with a separate second pair of connecting lines of separate adapters, additional a valve elements movable in said terminal board for each of said first pair of connecting lines, and locking means connected to at least two of said valve elements for precluding movement of one of said at least two valve elements when movement of the other of said at least two valve elements is permitted.

9. A device according to claim 8, wherein said locking means comprises a recess in each of said valve elements, an engagement wedge for movement into each of said recesses and a rocker arm connected to said engagement wedges for engaging one of said engaging wedges into one of said recesses at a time.

10. A device according to claim 1, wherein said alignment means comprises a projection of said adapter and a further recess in said terminal board for receiving said projection and aligning said first pair of connecting lines with said second pair of connecting lines.

11. A device according to claim 1, wherein said adapter engages with said second engagement surface on said first engagement surface over said terminal board, a remainder of said equipment unit connected to said adapter depending therefrom and downwardly past said terminal board.

12. A device according to claim 11, including at least one elastic stop member connected to said terminal board for abutment against remainder of said equipment unit.

13. A device according to claim 1, including sealing means for sealing a connection between said aligned first and second pair of connecting lines positioned at said first engagement surface.

14. A device according to claim 13, wherein said sealing means comprises an elastic O-ring at an end of each of said first pair of connecting lines at said first engagement surface.

* * * * *